(12) United States Patent
Moosmüller et al.

(10) Patent No.: US 8,049,895 B2
(45) Date of Patent: Nov. 1, 2011

(54) INSTRUMENT FOR MEASURING PARTICLE PARAMETERS

(75) Inventors: Hans Moosmüller, Reno, NV (US); W. Patrick Arnott, Reno, NV (US)

(73) Assignee: Board of Regents of the Nevada System of Higher Education, on behalf of the Desert Research Institute, Reno, NV (US)

( * ) Notice: Subject to any disclaimer, the term of this patent is extended or adjusted under 35 U.S.C. 154(b) by 0 days.

(21) Appl. No.: 12/533,658

(22) Filed: Jul. 31, 2009

(65) Prior Publication Data
US 2010/0020323 A1    Jan. 28, 2010

Related U.S. Application Data

(63) Continuation of application No. 11/550,352, filed on Oct. 17, 2006, now abandoned.

(60) Provisional application No. 60/727,750, filed on Oct. 17, 2005.

(51) Int. Cl.
*G01N 21/00* (2006.01)

(52) U.S. Cl. ............... 356/438; 250/559.16; 250/574; 250/564; 356/336; 356/446; 382/133; 382/134

(58) Field of Classification Search .......... 356/336–343, 356/438, 446; 250/559.16–559.18, 564, 250/573, 574; 382/133, 134
See application file for complete search history.

(56) References Cited

U.S. PATENT DOCUMENTS

| 4,942,305 A * | 7/1990 | Sommer .................. 356/343 |
| 6,606,157 B1 * | 8/2003 | Kaye et al. ................ 356/336 |

* cited by examiner

*Primary Examiner* — Michael A Lyons
*Assistant Examiner* — Iyabo S Alli
(74) *Attorney, Agent, or Firm* — Ryan A. Heck; UNR-DRI Technology Transfer Office (57) ABSTRACT

Values for one or more particle properties, such as an aerosol asymmetry parameter g, can be measured directly using a detector that measures scattered light. The detector can comprise two or more diffusers coupled to optical sensors responsive to scattered light that is incident on the surfaces of the diffusers. One or more weighing functions can be obtained based on diffuser geometry. In an example, the diffusers correspond to quadrants of a circular toroid.

23 Claims, 9 Drawing Sheets

INSTRUMENT FOR MEASURING PARTICLE PARAMETERS

CROSS REFERENCE TO RELATED APPLICATIONS

This application is a Continuation of U.S. patent application Ser. No. 11/550,352, filed Oct. 17, 2006 now abandoned, and entitled "INSTRUMENT FOR MEASURING PARTICLE PARAMETERS", which in turn claims the benefit of U.S. Provisional Patent Application No. 60/727,750, titled "INSTRUMENT FOR MEASURING THE AEROSOL ASYMMETRY PARAMETER (G)," filed Oct. 17, 2005, both of which are incorporated herein by reference.

FIELD

The disclosure pertains to measurements of aerosol parameters such as an aerosol asymmetry parameter.

BACKGROUND

Radiative transfer models can be used to model the transfer of electromagnetic radiation (e.g., sunlight) in the atmosphere and can be useful for understanding and modeling phenomena such as global climate change. One factor these models consider is how much light is absorbed or reflected by particles suspended in the atmosphere, thereby contributing to radiative forcing. Such particles include aerosols, which are generally no larger than about 10 µm in diameter. Aerosols may be generated naturally, for example by wild fires, dust entrainment, volcanic eruptions, etc., or they may be a result of human activity, such as the burning of fossil fuels. The amount of light that an aerosol or other particle absorbs or scatters depends on factors such as the size, shape and composition of the particle.

The angular distribution of light scattered by aerosol particles is useful in determining the aerosol contribution to radiative forcing. This angular distribution is commonly parameterized into a single value, the asymmetry parameter g, for use in large-scale radiative transfer models. This asymmetry parameter g is used to describe the angular distribution or phase function of aerosol scattering, often according to the single-parameter Henyey-Greenstein phase function. See, e.g., Henyey, L. C. and J. L. Greenstein "Diffuse Radiation in the Galaxy," *Astrophys. J* 93, 70-83 (1941); and Cornette, W. M. and J. G. Shanks, "Physically Reasonable Analytic Expression for the Single-Scattering Phase Function," *Appl. Opt.* 31, 3152-3160 (1992). According to this function, the asymmetry parameter g is defined as an intensity-weighted average cosine of the scattering angle, $$g = \frac{1}{4\pi} \int_{4\pi} d\Omega P(\theta)\cos(\theta) \quad (1)$$

$$= \frac{1}{4\pi} \int_0^\pi d\theta P(\theta)\sin(\theta)\cos(\theta) \int_0^{2\pi} d\phi$$

$$= \frac{1}{2} \int_0^\pi d\theta P(\theta)\sin(\theta)\cos(\theta),$$

wherein θ is an angle between a propagation direction of an incident light flux and a direction of propagation of a scattered light flux, and wherein P(θ) is a phase function giving an angular distribution of the scattered light. Values of g range from −1 for pure backscattering to +1 for pure forward scattering.

Rather than being measured directly, the asymmetry parameter g is typically estimated indirectly from other aerosol parameters. See, e.g., Andrews et al., "Comparison of Methods for Deriving Aerosol Asymmetry Parameter," *J. Geophys. Res.*, 111, doi: 10.1029/2004JD005734 (2006). Cloud integrating nephelometers and polar nephelometers have been used for the measurement of g for large particles (e.g., large relative to the wavelength of incident light that the particles scatter), including water drops and ice crystals. Modifications to an integrating nephelometer to measure aerosol g directly have been proposed previously. See, e.g., Gayet, J. F. et al. "A New Airborne Polar Nephelometer for the Measurements of Optical and Microphysical Cloud Properties. Part I: Theoretical Design" *Ann. Geophysicae* 15, 451-459 (1997); Gerber et al. "Nephelometer Measurements of the Asymmetry Parameter, Volume Extinction Coefficient, and Backscatter Ratio in Arctic Clouds," *J. Atmos. Sci.* 57, 3021-3034 (2000); and Heintzenberg, J. and R. J. Charlson, "Design and Application of the Integrating Nephelometer: A Review," *J. Atmos. Ocean. Technol.* 13, 987-1000 (1996). Cloud integrating nephelometers typically cannot measure aerosol properties, and polar nephelometers are typically complex and expensive.

SUMMARY

Values for one or more particle properties, e.g., an aerosol asymmetry parameter g, can be measured directly using a detector assembly designed to measure light scattered by one or more particles. The detector assembly can comprise two or more diffusers coupled to respective optical sensors to respond to scattered light that is incident to surfaces of the diffusers. One or more weighing functions can be selected based on the geometry of the diffuser and based on one or more radiative transfer functions. Sensor signals can be processed according to the weighing function to estimate a selected particle parameter.

According to representative examples, apparatus for radiation scattering measurements comprise a plurality of diffusers situated along a detection axis and configured to receive respective portions of a light flux scattered from an optical axis that is substantially perpendicular to the detection axis. Each of the diffusers is coupled to a respective light sensor. In some examples, at least one optical barrier is coupled to the plurality of diffusers so that the diffusers are substantially optically isolated from each other. In other representative examples, the plurality of diffusers is defined by respective longitudinal portions of a circular toroidal solid that consists essentially of a translucent material such as TEFLON. In some examples, each of the diffusers is substantially a quadrant of a circular toroidal solid.

In further examples, each of the diffusers is defined by respective interior longitudinal portions of a substantially circular toroidal shell (or longitudinal segment thereof), wherein the shell includes a scattering exterior surface. In some examples, each of the diffusers is defined by a quadrant of the toroidal shell. In other examples, the plurality of diffusers is defined by respective quadrants of a longitudinal segment of a circular cylinder. In additional examples, at least one optical barrier is coupled to the plurality of diffusers so that the diffusers are substantially optically isolated from each other.

According to further examples, a second plurality of diffusers is situated along a second detection axis that is substantially perpendicular to the optical axis. These diffusers are configured to receive respective portions of a light flux scattered from the optical axis. The first and second detection axes are substantially situated in a plane perpendicular to the optic axis, and each of the diffusers of the second plurality of diffusers is coupled to a respective light sensor. In some examples, the first detection axis and the second detection axis are substantially parallel, substantially perpendicular, or at an angle of about 30 degrees or 45 degrees. In some representative examples, a processor is coupled to the plurality of sensors and is configured to determine a scattering parameter. In some particular examples, the scattering parameter is an aerosol asymmetry parameter or a scattering coefficient.

Methods of measuring an aerosol scattering parameter comprise receiving a light flux scattered by an aerosol at a plurality of diffusers, and estimating magnitudes of portions of the scattered light flux received by each of the plurality of diffusers. The scattering parameter is determined based on the estimates. In some examples, an exterior of at least one of the diffusers is selectively patterned based on a scattering parameter to be estimated. According to representative examples, the diffusers consist essentially of a light scattering solid.

Measurement apparatus for determining a light scattering characteristic comprise a plurality of diffusers coupled to respective sensors, wherein the sensors are coupled to produce respective sensor signals based on a scattered light flux. The diffusers are configured to provide a selected weighing function response. A processor is coupled to receive the sensor signals and determine the scattering characteristic. In some examples, the diffusers are based on corresponding volumes of a light scattering material or cavities defined at least in part by a light scattering surface. In a representative example, the scattering characteristic is a scattering coefficient or an aerosol asymmetry parameter.

The foregoing and other objects, features, and advantages of the disclosed technology will become more apparent from the following detailed description, which proceeds with reference to the accompanying figures.

DETAILED DESCRIPTION

As used in this application and in the claims, the singular forms "a," "an," and "the" include the plural forms unless the context clearly dictates otherwise. Additionally, the term "includes" means "comprises." Further, the term "coupled" means electrically, electromagnetically, mechanically, or optically coupled or linked and does not exclude the presence of intermediate elements between the coupled items.

Although the operations of example embodiments of the disclosed method are described in a particular, sequential order for convenient presentation, it should be understood that disclosed embodiments can encompass an order of operations other than the particular, sequential order disclosed. For example, operations described sequentially may in some cases be rearranged or performed concurrently. Moreover, for the sake of simplicity, the attached figures may not show the various ways (readily discernable, based on this disclosure, by one of ordinary skill in the art) in which the disclosed system, method, and apparatus can be used in conjunction with other systems, methods, and apparatus. Various embodiments and elements of the embodiments of the technologies described herein can, in some cases, be used in combination with other embodiments. Additionally, the description sometimes uses terms like "produce" and "provide" to describe the disclosed method. These terms are high-level abstractions of the actual operations that can be performed. For example, "providing" a component can mean making that component available for use or configuration with additional components. The actual operations that correspond to these terms can vary depending on the particular implementation and are, based on this disclosure, readily discernible by one of ordinary skill in the art.

In the examples described herein terms such as "light" and "light flux" are used to describe both incident and scattered optical radiation. While wavelengths of particular interest with the disclosed technology range from about 200 nm to about 20 µm, other wavelengths can be used, and "light" is used herein to generally refer to propagating electromagnetic radiation of any wavelength.

Representative examples are described below based on cylindrical diffusers and toroids having a circular cross section. As used herein, a toroid is defined as a solid defined by a surface of revolution obtained by rotating a closed plane curve about an axis parallel to a plane and that does not intersect the curve. A circular toroid is based on rotation of a circle. Thus, in some examples, a toroid can have a circular, elliptical, or rectangular cross section, and can be based on revolution of a circle, ellipse, or rectangle about the appropriate axis. For convenience, examples based on circular toroids are described. As used herein, a detection axis is a straight or curved axis along which one or more radiation diffusers are aligned. A detection axis is generally oriented, during scattering measurements, to be substantially perpendicular to a direction of propagation of a light flux to be scattered and received by the diffusers, but other orientations can be used. The detection axes of a circular cylinder and a circular toroid are axes that pass through and along a center of their circular cross sections. Radiation diffusers typically are defined so as to extend along such detection axes. Segments of cylinders or toroids that extend along such detection axes are referred to herein as longitudinal segments or sections.

In a typical example based on a circular toroid, the toroid is divided into four separate but substantially equal portions ("quadrants") that are defined by surfaces of rotation obtained based on rotation of the quadrants of the corresponding circular cross section. Two inner quadrants are situated so as to face toward an optical axis and two outer quadrants are situated to face away from the optical axis. This configuration is convenient, and other arrangements can be used. In other examples, one or more longitudinal segments of a toroid or cylinder are divided into quadrants that extend along the detection axis and such quadrants are referred to herein as longitudinal quadrants.

Figure 1:
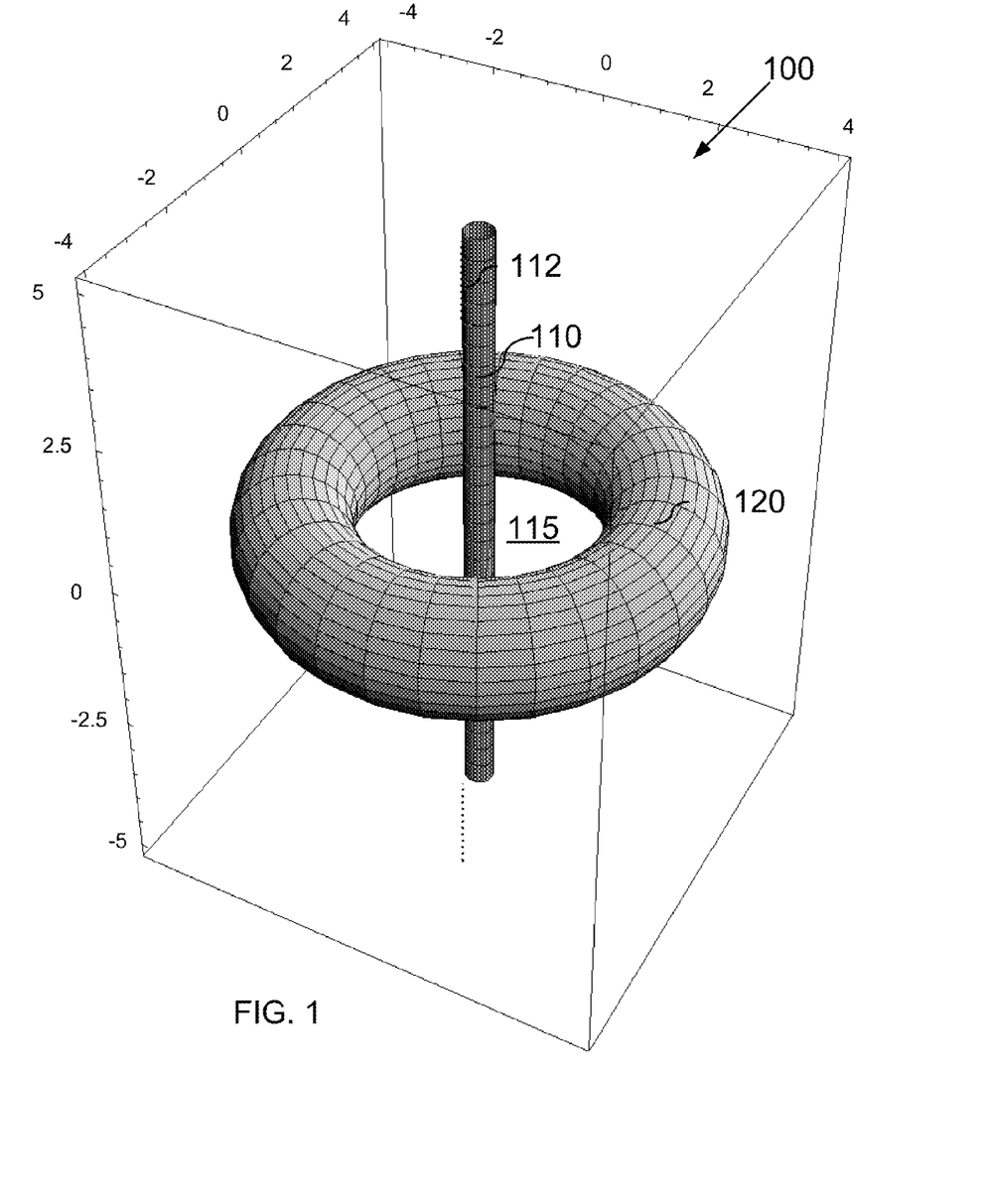
FIG. 1 is a perspective view of one embodiment of a detection system.
Figure 2:
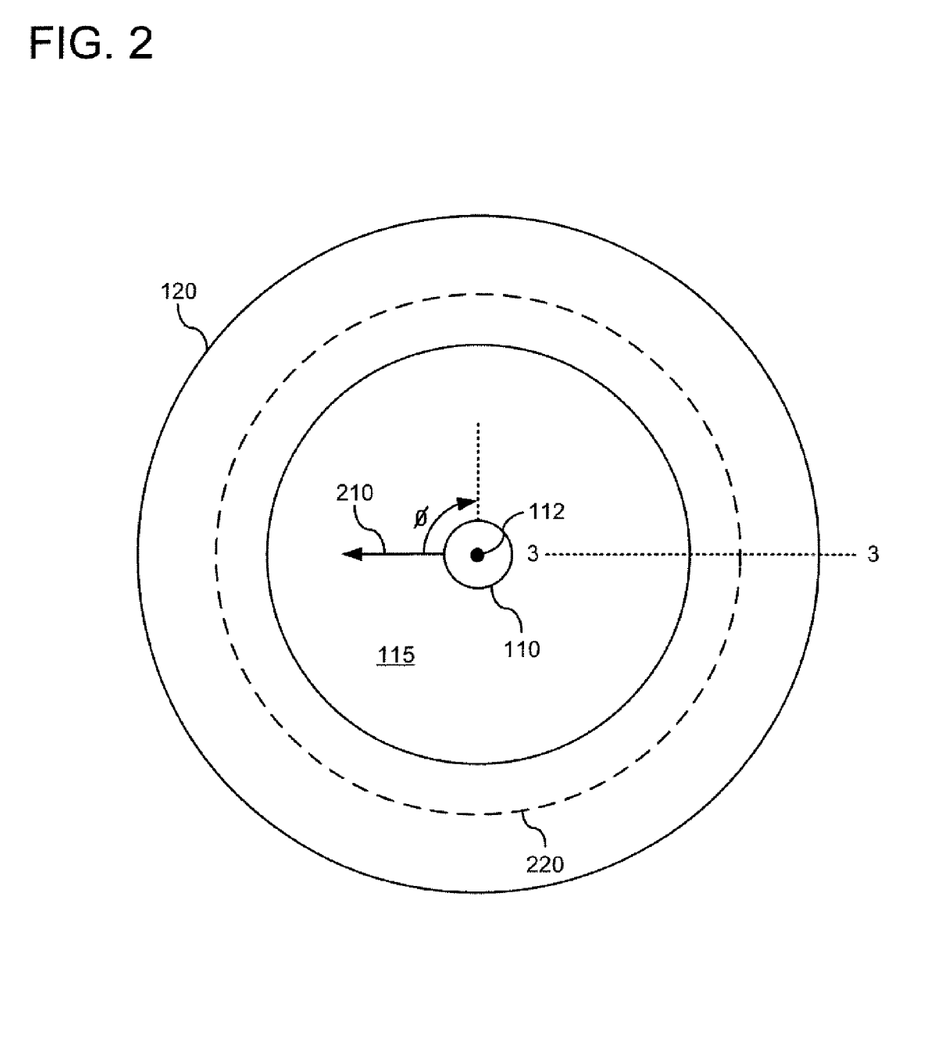
FIG. 2 is a plan view of the detection system of FIG. 1.

FIG. 1 shows a perspective view of one embodiment of a detection system 100 in which a light source (not shown) is configured to direct a light flux 110 (e.g., a laser beam) so as to propagate along an optical axis 112. A plurality of diffusers can be defined by a circular toroidal surface 120 having a central aperture 115 through which the light flux 110 is transmitted. Diffusers can be defined by dividing the surface 120 and/or a volume defined by the surface 120 into one or more portions. Typically, the surface is divided into four quadrants. In some examples, diffusers are defined by longitudinal segments of a toroid such as segment portions that extend about the axis 112 by angles of for example, 270 degrees, 180 degrees, 90 degrees, 45 degrees, or other angles between 0 and 360 degrees. In other examples, diffusers can be defined by surfaces of other shapes. For example, elliptical, ovoid, rectangular, octagonal or other regular or irregular shaped toroids can be used. In some examples, two or more separate surfaces are used to define diffusers. Typically, such surfaces are situated directly opposite each other with respect to the axis 112, or at angles of 90 degrees or 45 degrees about the axis 112. For example, portions of the surface 120 can be used, and the entire toroid is unnecessary. FIG. 2 is a plan view of the detection system 100 of FIG. 1. As shown in FIG. 2, a direction of propagation 210 of a scattered light flux has an azimuthal angle $\phi$, defined as an angle of rotation around the axis 112. The surface 120 extends along a detection axis 220.

Figure 3:
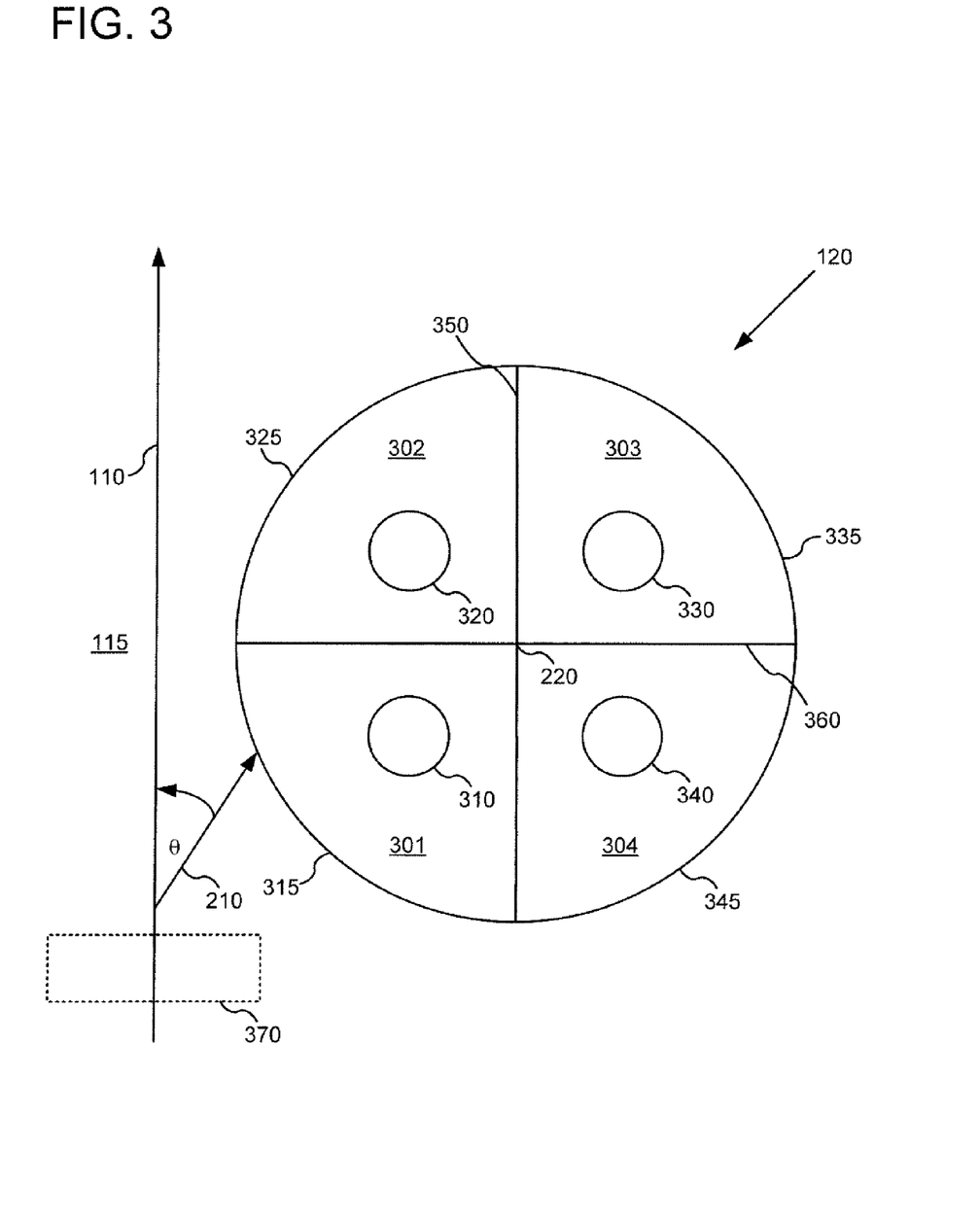
FIG. 3 is a cross-sectional view of a detection system of FIGS. 1-2.

A cross-sectional view of the surface 120 is shown in FIG. 3. The surface 120 defines a plurality of diffusion regions ("diffusers") 301, 302, 303, 304 that extend along the axis 220. In other examples, fewer or more diffusers can be provided. In some embodiments, the diffusers comprise cavities defined by the surface 120 and the surface 120 is provided with a diffusive or light scattering coating or other treatment, while in other embodiments, the diffusers are defined with one or more transparent, translucent, or scattering materials provided in the regions 301, 302, 303, 304, such as, for example, TEFLON or other light scattering solids. Each of the regions 301, 302, 303, 304 can be coupled to respective optical sensors 310, 320, 330, 340, such as, for example, photomultipliers (PMTs), avalanche photodiodes, PIN photodiodes, or other photodetectors.

The optical sensors 310, 320, 330, 340 can be configured to produce respective electrical signals $S_1$, $S_2$, $S_3$, $S_4$ based on optical powers $PQ_i$ incident on the respective outer surfaces 315, 325, 335, 345, wherein i=1, 2, 3, 4. Boundaries between the diffusers 301-304, such as boundaries 350, 360, can be configured to provide optical isolation among the optical sensors 310, 320, 330, 340 and the diffusers 301-304. Typically the boundaries 350, 360 are substantially opaque. For example, one or more metallic layers or metal sheets or foils can be used to separate the regions. The surfaces of such metal layers can be provided with a light scattering coating or a light scattering layer so that any light flux within a region tends to be more uniformly distributed. The diffusers 301-304 can be conveniently bonded together to form a unitary assembly with or without opaque or other boundary materials.

Outer surfaces 315, 325, 335, 345 of the diffusers 301, 302, 303, 304 can be provided with a scattering material that generally exhibits Lambertian scattering. Typical materials include TEFLON, spectralon, and frosted glass. In one example, the diffusers can be formed as sections of a light scattering or translucent tube made of, for example, TEFLON. In other embodiments, the outer surfaces 315, 325, 335, 345 can comprise a continuous surface of a tube. Use of scattering materials tends to provide that scattered optical power within a diffuser and directed to the associated light sensor is proportional to the power incident to the diffuser in a manner similar to the "cosine detector" that can be used in reciprocal nephelometers. In addition, surfaces of boundaries 350, 360 can be coated with a scattering material similar to that of the outer surfaces 315, 325, 335, 345, or with another scattering material such as barium sulfate or zinc oxide.

While the surface 120 is shown in FIG. 3 as having a generally circular cross-section, in other embodiments, the surface 120 can have cross-sections of other shapes (e.g., ovoid, octagon, etc.). As will be explained below, calibration techniques can compensate for shape selection and/or irregularities. Additional embodiments can feature detectors with multiple cross-sections having multiple, different shapes.

In use, a particle or distribution of particles (not shown) in, above, or below the center opening 115 can scatter some of the light from light flux 110 toward the surface 120. In FIG. 3, the scattered light propagates along an axis 210 that diverges from the propagation direction of the light flux 110 at a scattering angle $\theta$.

Weighing factors and surface shapes for surfaces and diffusers such as illustrated in FIGS. 1-3 can be obtained based on the following analysis. Generally, a quantity of scattered light incident on an outer surface of a diffuser and that can reach as associated detector is estimated based on the shape and placement of the diffuser and the scattering or diffusing properties of the diffuser. Based on geometrical considerations (shape and placement of the diffusers 301-304), scattered power $PQ_i$ incident on an outer surfaces of a region i=1, 2, 3, 4 (i.e., the diffusers 301-304) can be calculated by integrating over the scattering angle $\theta$. For example, for a detector with a circular cross-section with a surface partitioned into four quadrants, scattered power $PQ_i$ can be calculated as:

$$PQ_1 = C_P \left[ \int_0^{\pi/2} d\theta P(\theta)[\sin(\theta) + \cos(\theta)] + \int_{\pi/2}^{\pi} d\theta P(\theta)[1 + \cos(\theta)] \right] \quad (2)$$

$$PQ_2 = C_P \left[ \int_0^{\pi/2} d\theta P(\theta)[1 - \cos(\theta)] + \int_{\pi/2}^{\pi} d\theta P(\theta)[\sin(\theta) - \cos(\theta)] \right] \quad (3)$$

$$PQ_3 = C_P \left[ \int_{\pi/2}^{\pi} d\theta P(\theta)[1 - \sin(\theta)] \right] \quad (4)$$

$$PQ_4 = C_P \left[ \int_0^{\pi/2} d\theta P(\theta)[1 - \sin(\theta)] \right] \quad (5)$$

wherein P(θ) is a scattering phase function and $C_P$ is a proportionality factor including light flux (laser power) $P_{Laser}$ and a scattering coefficient σ as:

$$C_P = C_0 P_{Laser} \sigma. \quad (6)$$

A detector signal $S_i(\theta)$ for an optical sensor associated with diffuser i is proportional to the incident scattered power $PQ_i$ as:

$$S_i = C_S PQ_i, \quad (7)$$

wherein $C_S$ is a proportionality constant. For the measurement of $C_S C_P$, a detector signal $S_\sigma$ can be defined as:

$$S_\sigma = 2\pi[S_1 + S_2 - (S_3 + S_4)] \quad (8)$$

or $$S_\sigma = 4\pi C_S C_P \int_0^\pi d\theta \sin(\theta) P(\theta) = 2 C_S C_P. \quad (9)$$

Equation 9 describes a reciprocal nephelometer. $C_P$ is a function of the scattering coefficient σ that can be determined, for example, after a common nephelometer calibration is performed based on the surface 120 using two media with different and known scattering coefficients.

A total detector signal $S_{raw}$ can be defined by combining multiple detector signals as:

$$S_{raw} = \frac{S_1 - S_2 + S_3 - S_4}{S_\sigma} = \frac{S_1 - S_2 + S_3 - S_4}{2\pi(S_1 + S_2 - S_3 - S_4)} \quad (10)$$

Division by $S_\sigma$ eliminates the dependence on laser power and on the scattering coefficient (by eliminating the factor $C_S C_P$) yielding:

$$S_{raw} = \int_0^{\pi/2} d\theta P(\theta)[-1 + \sin(\theta) + \cos(\theta)] + \int_{\pi/2}^\pi d\theta P(\theta)[1 - \sin(\theta) + \cos(\theta)] \quad (11)$$

The detector signal $S_{raw}$ can also be written as:

$$S_{raw} = \int_0^\pi d\theta P(\theta) g_w(\theta), \quad (12)$$

where $g_w(\theta)$ is defined as:

$$g_w(\theta) = \cos(\theta) + \text{sgn}(\theta - \pi/2)[1 - \sin(\theta)] \quad (13)$$

and "sgn" is the "sign" function, defined as −1 for negative arguments, 0 for 0 arguments and +1 for positive arguments. Equation 13 is similar to the definition of g given above as:

$$g = \frac{1}{2} \int_0^\pi d\theta P(\theta) \sin(\theta) \cos(\theta) \quad (14)$$

if $g_w(\theta)$ is approximately equal to $\sin(\theta)\cos(\theta)$.

Figure 4:
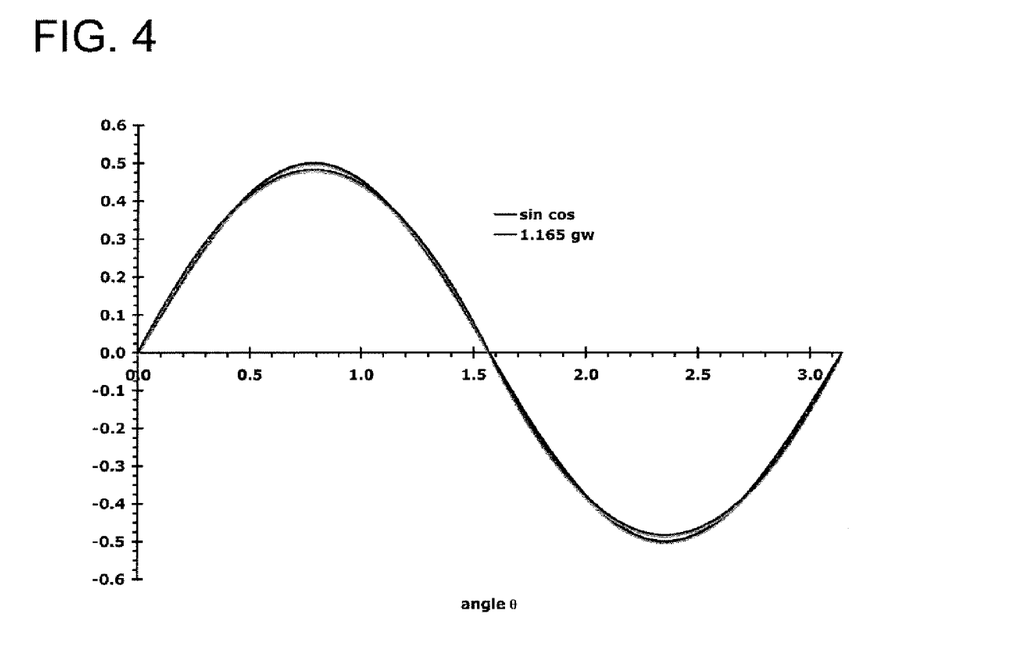
FIG. 4 is a graph showing a comparison of a function sin (θ) cos (θ) and an instrumental weighing function obtained using the detector system of FIGS. 1-3.

Defining a retrieved (i.e., measured) asymmetry parameter $g_{retr}$ with an appropriate normalization constant as $$g_{retr} = \frac{1.165}{2} S_{raw} = \frac{1.165}{2} \left[ \int_0^\pi d\theta P(\theta) g_w(\theta) \right], \quad (15)$$

yields a close match between 1.165 $g_w(\theta)$ and $\sin(\theta) \cos(\theta)$, as can be seen in FIG. 4. Equation 15 (used in conjunction with Equation 10) defines a weighing function for measurements recorded by the optical sensors in the various regions of a detector.

Similarly, weighing functions can be derived for detectors having cross-sections other than generally circular cross-sections and for detectors having more than four regions. Weighing functions can also be derived using other radiative transfer functions.

Figure 5:
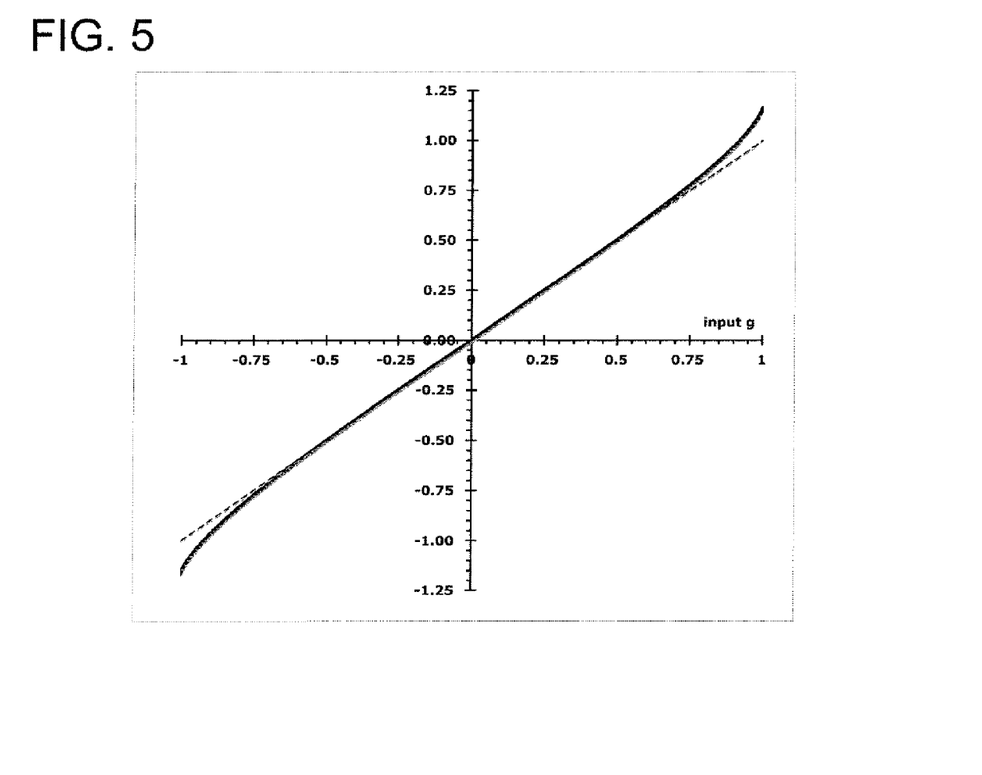
FIG. 5 is a graph showing a comparison of measured values of g with input values of g.
Figure 6:
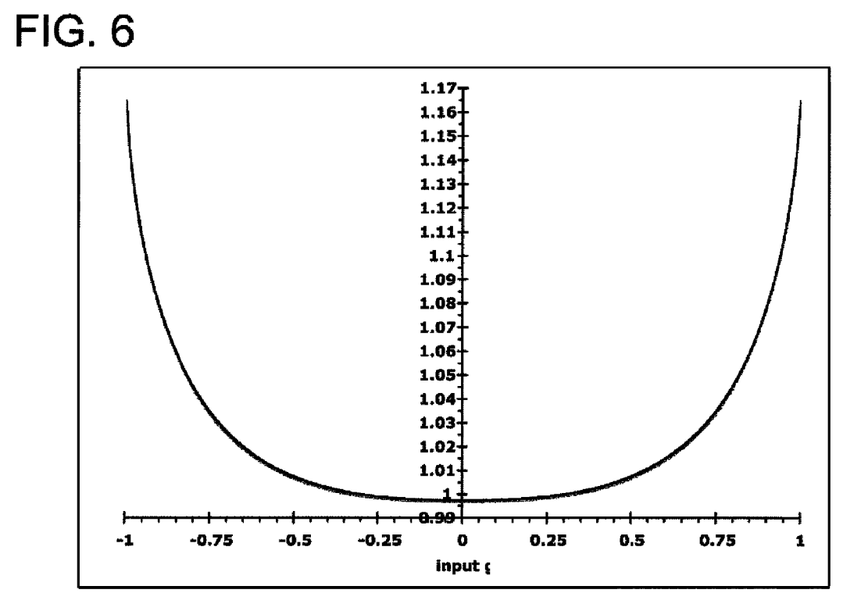
FIG. 6 is a graph showing a ratio of measured values of g to input values of g.

Values of the asymmetry parameter g produced using Equation 15 can be compared to those produced using the Henyey-Greenstein phase function, which provides $$P_{HG}(\theta) = \frac{1 - g^2}{[1 + g^2 - 2g\cos(\theta)]^{3/2}}, \quad (16)$$

and which can be used to describe the angular distribution of the scattering. Using the equation for the measured asymmetry parameter $g_{retr}$, the asymmetry parameter as measured by the instrument can be calculated and compared to the input asymmetry parameter g used in the Henyey-Greenstein phase function. This comparison is shown in FIG. 5, where the dashed line indicates the ideal situation of one-to-one correspondence of input g and measured g. FIG. 6 shows the ratio of retrieved g and input g, indicating that the retrieved g can be up to 16.5% larger than the input g in the extreme situations of g≈−1 and g≈+1. For ambient aerosols, g tends to be between 0.5 and 0.8, and for this range the retrieval error is smaller than about 4%.

Figure 7:
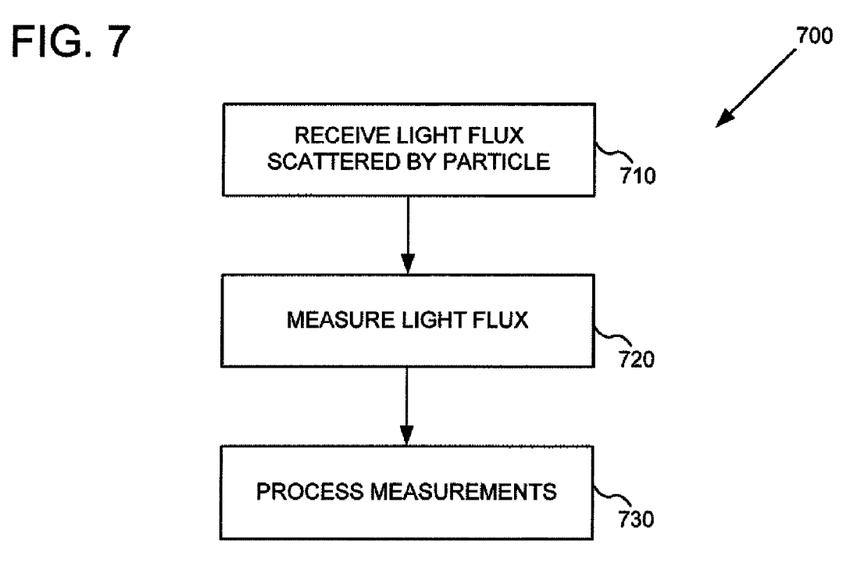
FIG. 7 is a block diagram of a representative method of measuring particle properties.

FIG. 7 is a block diagram of one embodiment of a method 700 for measuring aerosol scattering properties using, for example, a plurality of diffusers such as those defined by the surface 120 of FIGS. 1-3. A plurality of diffusers receive respective portions of a light flux scattered by an aerosol in step 710, and a detection signal associated with each of the portions is obtained in a step 720. The detection signals are processed according to a weighing function derived from a radiative transfer function in a step 730. For example, Equation 15 can be used to define a weighing function, and detection signals can be combined to obtain an aerosol asymmetry factor.

The diffusers defined by, for example, the surface 120 of FIGS. 1-3 have a symmetry that can allow detection of scattered light independent of the scattered light's azimuthal angle φ. In such an embodiment, integration over φ yields 2π. However, in some examples, scattering is a function of azimuthal angle. For example, a polarized light flux is generally asymmetrically scattered. In some examples, input light flux polarizations can include, but are not limited to, linear, circular, random, pseudorandom, and elliptical. A desired polarization can be provided by, for example, a polarizer 370, as shown in FIG. 3, or a retardation plate can be used to modify a polarization state of a polarized input light flux. In particular embodiments, laser beam polarization can be modified to record measurements as a function of beam polarization. This can provide information on the shape of aerosols. To fully sample scattering from a linearly polarized light flux, diffuser sets are preferably situated along mutually perpendicular axes that are also perpendicular to the propagation direction of the light flux and at angles of 45 degrees with respect to the polarization direction.

Figure 8:
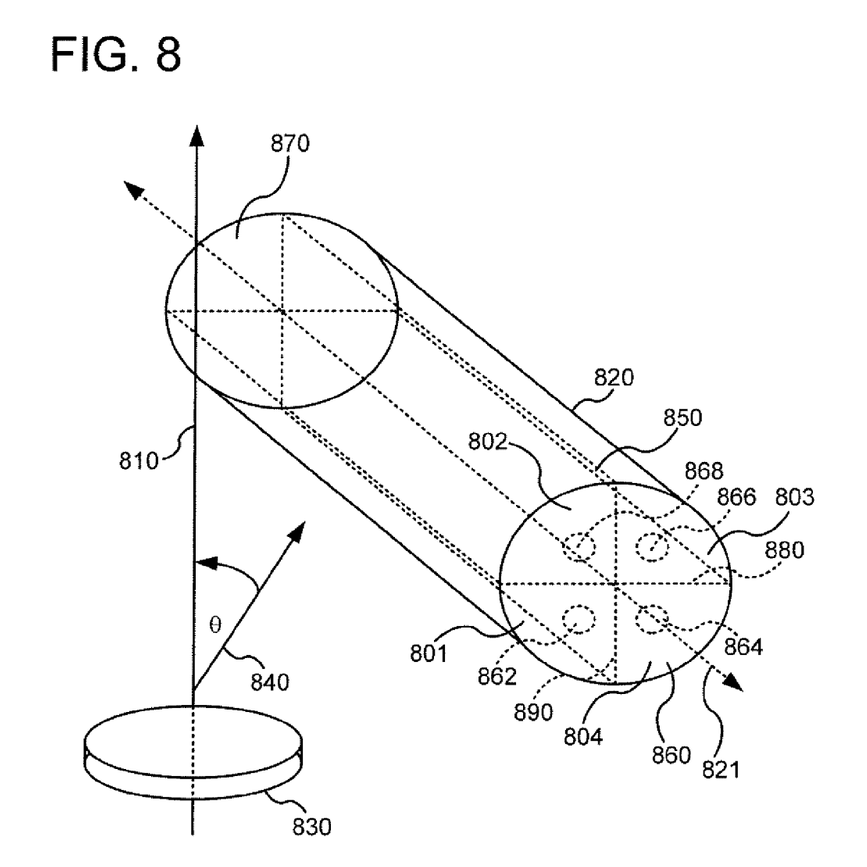
FIG. 8 is a perspective view of one embodiment of a detection system that includes diffusers defined as longitudinal quadrants of a cylindrical segment.

In some embodiments, the toroidal detector can be replaced with a short toric segment that can be approximated by a short cylinder. For example, FIG. 8 shows a perspective view of one embodiment that includes a cylindrical section 820 of length l that defines a plurality of diffusers 801, 802, 803, 804. An incident light flux propagates along an optical axis 810 that is displaced from the section 820. A state of polarization of the light flux can be selected using a polarizer, retardation plate, or other polarization control device 830. An axis 821 of the section 820 (a detection axis) is substantially perpendicular to the optical axis 810. An aerosol (not shown) scatters light from the axis 810 along an axis 840 at a scattering angle θ. In some embodiments, an exterior surface 850 of the section 820 is provided with a white scattering material that generally exhibits Lambertian scattering. In some embodiments, the interior of the section 820 can be arranged in quadrants in a manner similar to that of FIG. 3. For example, the interior of the section 820 can be divided into two or more regions by boundaries 880, 890 to define the diffusers 801-804. In other embodiments, the interior of the section 820 defines fewer or more than four diffusers. Generally, a larger number of diffusers can provide additional information.

Figure 9:
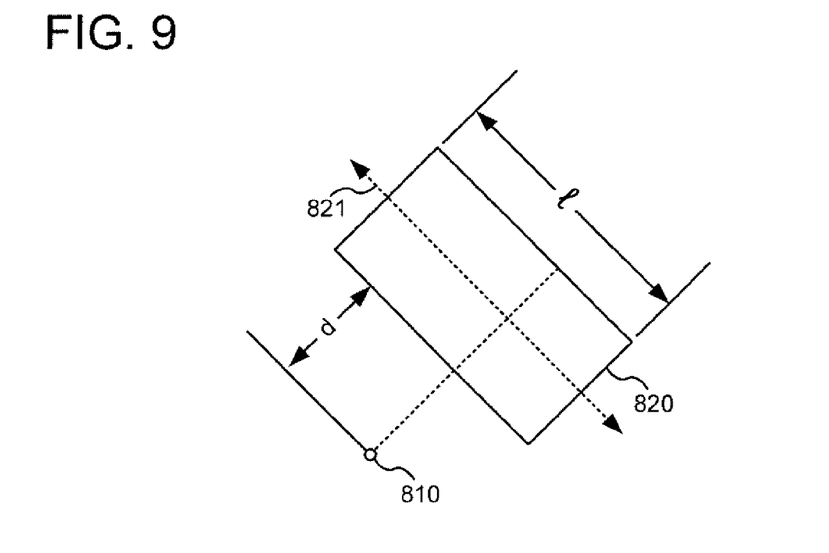
FIG. 9 is a plan view of the detection system of FIG. 5.

In additional embodiments, one or more end caps 860, 870 are provided with an opaque material, and opaque layers such as a metal foil or metal plate are provided at boundaries 880, 890. In some embodiments end caps 860, 870 and/or the opaque layers at boundaries 880, 890 are coated partially or entirely with a diffusely scattering material (e.g., barium sulfate). Optical sensors 862, 864, 866, 868 and/or fiber optics coupled to optical sensors can be mounted to one or more of the end caps 860, 870 in association with the diffusers. FIG. 9 is a plan view illustrating a location of the optical axis 810 along which an input light flux propagates with respect to the section 820 of length l that is positioned a distance d from the optical axis 810. Typically, the analysis of Equations 1-16 can be used to describe measurements based on the arrangement of FIGS. 8-9, particularly if the length l is short relative to the distance d from the optical axis 810 such that the cylindrical section approximates a section of a circular toroid. In some embodiments, ratios of l:d can be less than 0.1, 0.2, 0.5, or 1.0, and other values can be used. As shown in FIG. 9, the cylindrical section 820 is situated symmetrically with respect to an axis perpendicular to the optical axis 810 and an axis perpendicular to the detector axis 821, but other placements can be used. In further embodiments, two diffusers can be defined instead of four to obtain a scattering coefficient σ.

In some examples, measurements can be obtained at two or more wavelengths. For example, laser beams of different wavelengths can be sequentially switched. In other embodiments, simultaneous measurements at multiple wavelengths can be obtained by overlapping multiple laser beams with, for example, dichroic mirrors, and by modulating the multiple laser beams at different frequencies. Narrow band, frequency sensitive detection can be used to distinguish electrical signals associated with each of the laser beams.

Figure 10:
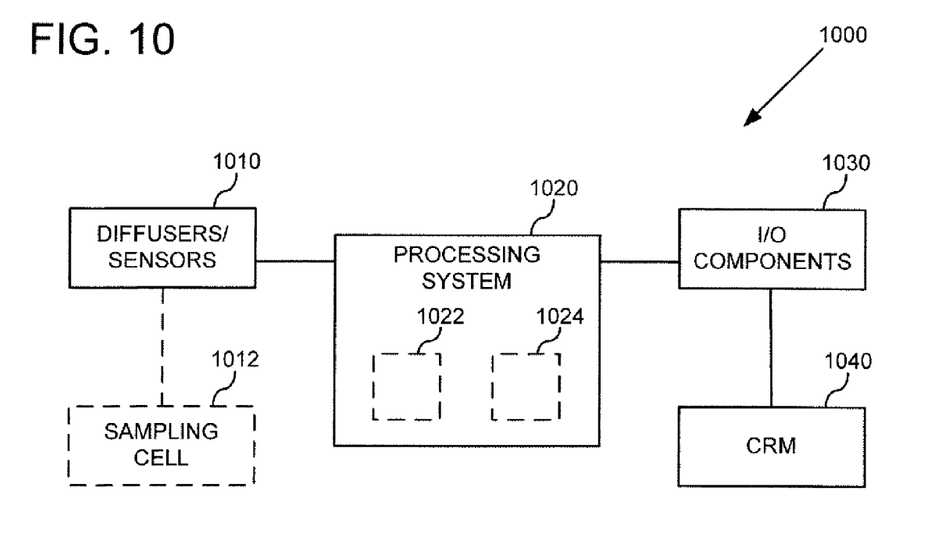
FIG. 10 is a block diagram of an exemplary measurement system.

In further embodiments, a multi-diffuser detector assembly can be incorporated into a measurement system. For example, FIG. 10 depicts a block diagram of one embodiment of an exemplary measurement system 1000. In some embodiments, the system 1000 comprises at least one set of diffusers/sensors 1010 configured to provide measurement signals and transmit the signals to a processing system 1020. In some embodiments, the processing system 1020 merely stores the data related to the signals, while in other embodiments analog components 1022 and/or digital components 1024 (e.g., a computer or a microprocessor) are provided to modify or otherwise process the data. For example, in some embodiments, one or more parameters such as the aerosol asymmetry parameter can be determined. The system 1000 can further comprise input/output components 1030 such as a monitor, a keyboard, a printer, a mouse and a storage device. The system 1000 can also be configured to read data from or write data to one or more computer-readable media (CRM) 1040. For example, in some embodiments instructions for the processing system 1020 can be read from the CRM 1040, while in additional embodiments measurements and results of processing measurements can be stored on the CRM 1040. In further embodiments, the set of diffusers/sensors 1010 can be used in conjunction with a sampling cell 1012. In some embodiments, the set of diffusers/sensors 1010 is inside the sampling cell 1012 along with a light source (not shown in FIG. 10), and in other embodiments it is external to the sampling cell 1012. In other embodiments the set of diffusers/sensors 1010 and the light source are exposed to ambient air. In such embodiments, the system 1000 can further comprise shielding (not shown) to help protect the set of diffusers/sensors 1010 from ambient light (e.g., sunlight). In other embodiments, the set of diffusers/sensors 1010 can be used as part of another instrument, such as a reciprocal nephelometer or a photoacoustic instrument.

Even in embodiments using identical optical sensors, the sensor/diffuser combinations can have slightly different sensitivities (quantum efficiencies) that can be compensated. In some embodiments, a control voltage for one or more PMTs is adjusted, or analog or digital processing of the sensor signals can be used.

Figure 11:
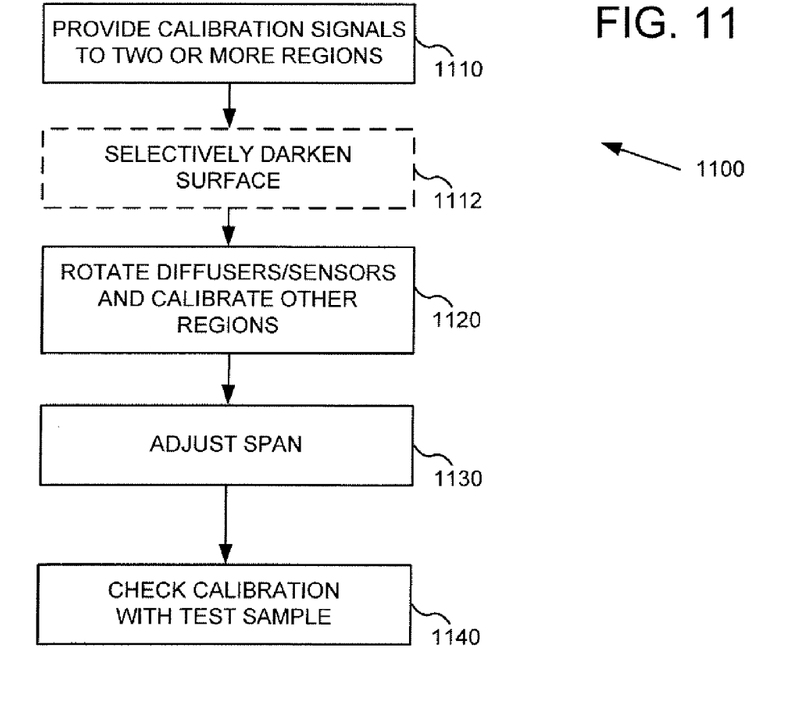
FIG. 11 is a block diagram of one embodiment of a technique for calibrating a detection system that includes a plurality of diffusers.

FIG. 11 shows a block diagram of one embodiment of a method 1100 for calibrating a detector. To perform calibration of a set of diffuser/sensors, the diffusers/sensors can be illuminated with a plane wave (e.g., a low-power expanded laser beam) propagating perpendicular to the surface 820 and perpendicular to one of the boundaries 880, 890 separating two or more regions. Thus two optical sensors can be calibrated to provide identical signals or nearly identical signals from a light input in a step 1110. This calibration can then be extended to optical sensors in other regions by rotating the assembly by π/2 radians about the detection axis (assuming the interior of the detector 820 comprises four regions) and calibrating the configuration relative to the previously calibrated configuration in a step 1120. To facilitate rotation, diffusers can be mounted on a rotation stage with the cylinder axis as the axis of rotation. During this calibration, the span of the instrument can also be adjusted to a maximum g-factor of +1 and a minimum of −1 in a step 1130. Once the instrument is calibrated, a simple calibration check can be done by filling the sample chamber with a test sample, such as a gas, preferentially one with high scattering coefficient (e.g., carbon dioxide), in a step 1140. Gases have an asymmetry parameter of zero, and thus the zero of the instrument can be checked. Those of ordinary skill in the art will recognize variations of the method 1100 for calibrating detectors with other shapes and other numbers of interior regions.

The angular instrument response of a detector can be further dependent on non-idealities, such as optical reflections from a optical interface at exterior surfaces of a diffuser set. During calibration, the diffuser/sensor assembly can be rotated continuously (or in small steps) about the optical axis to determine the angular response for comparison with, for example, an intended $\sin(\theta)\cos(\theta)$ response. The recorded response can then be adjusted to yield a selected response by, for example, selectively darkening a portion of an exterior surface of one or more diffusers. Such darkening can be provided by drawing one or more lines of varying width or by applying one or more patterns with a light-blocking or light-absorbing material. In this way, deviations from a selected response or weighing can be compensated or eliminated. For example, an angular response can be adjusted in this manner to provide a $\sin(\theta)\cos(\theta)$ response.

Figure 12:
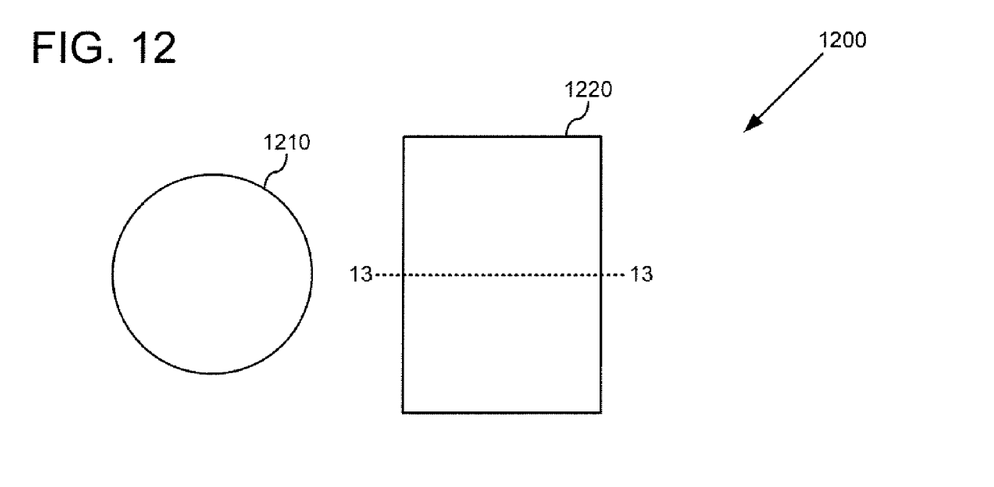
FIG. 12 is a plan view of a further embodiment of a detection system.
Figure 13:
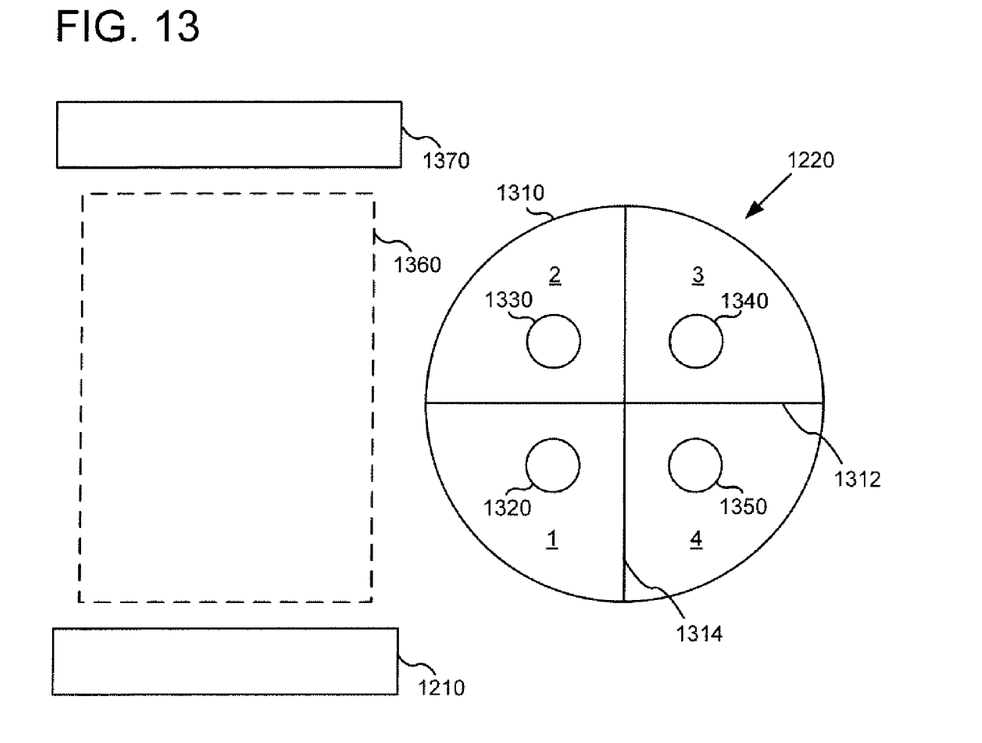
FIG. 13 is a cross-sectional view of the detection system of FIG. 12.

In still further embodiments, positions of the light source and the detector can be exchanged while obtaining functionality similar to that of other detector systems described herein. For example, FIG. 12 shows a plan view of an embodiment of an inverted detection system 1200 comprising an optical sensor 1210 and a cylinder 1220. FIG. 13 is a cross-sectional view of the detection system 1200 showing one embodiment of an interior of the cylinder 1220 that is divided into two or more regions by partitions 1312, 1314. A surface 1310 of the cylinder 1220 can comprise a white, strongly scattering material that generally exhibits Lambertian scattering. Instead of optical sensors, two or more light sources are distributed among two or more regions. For example, the cylinder 1220 contains light sources 1320, 1330, 1340, 1350. In some embodiments, these light sources are light emitting diodes (LEDs) and can be modulated at relatively high frequencies. Other light sources (e.g., lasers) can be used in combination with or instead of LEDs. Particle samples can be released into a view path region 1360 so as to scatter light from one or more light sources 1320, 1330, 1340, 1350 to the optical sensor 1210. A black object 1370 (e.g., beam trap or black hole) can be placed behind the view path region 1360, opposite the optical sensor 1210. In some embodiments, phase-sensitive or narrow band detection can be used to detect signals from LEDs at their modulation frequencies. This can yield multiple signals for calculating parameters such as the asymmetry parameter g and the scattering coefficient σ. In another embodiment an inverted system comprises a torus (instead of a cylinder) containing several light sources.

Figure 14:
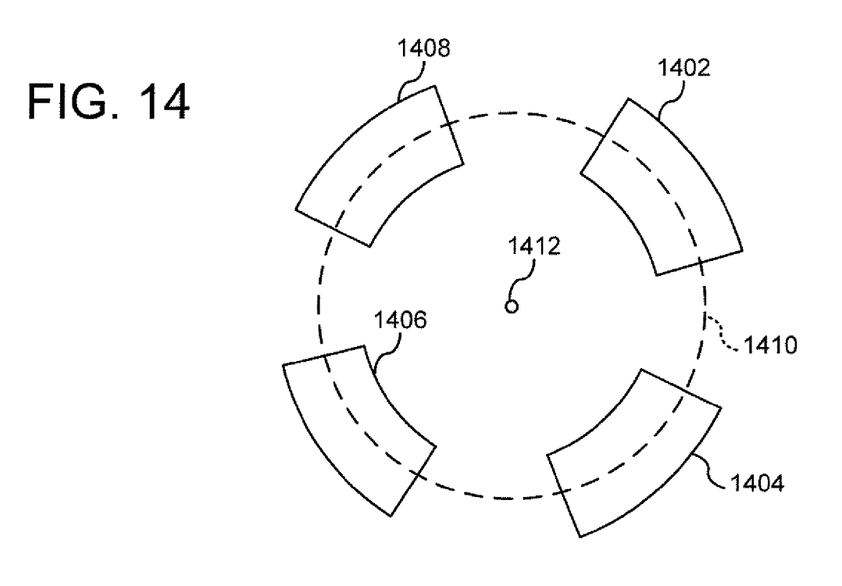
FIG. 14 is a plan view of a detection system in which diffusers are defined based on a plurality of toroidal segments.
Figure 15:
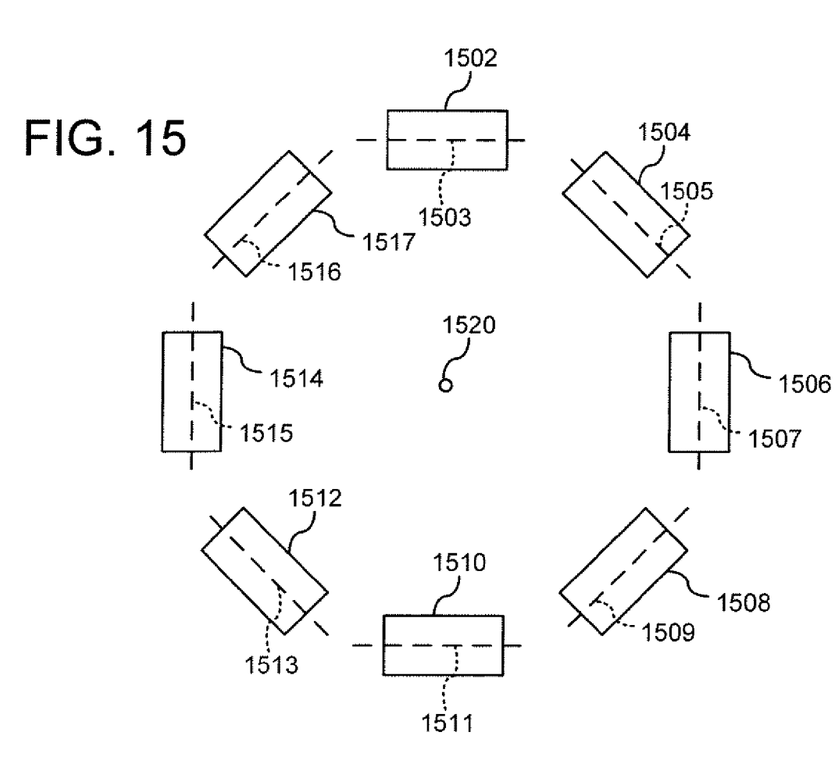
FIG. 15 is a plan view of a detection system in which diffusers are defined based on a plurality of cylindrical segments.

While diffusers based on longitudinal quadrants of a circular toroid can be used, in other examples, one or more sections of toroids or cylinders can be used. Referring to FIG. 14, toroidal sections 1402, 1404, 1406, 1408 that define respective sets of diffusers are situated along a detection axis 1410 and about an optical axis 1412. Each of the toroidal sections can be divided into longitudinal quadrants that define the diffusers. More or fewer toroidal sections can be used, but the arrangement of FIG. 14 can be convenient for use with a polarized light flux. Referring to FIG. 15, cylindrical sections 1502, 1504, 1506, 1508, 1510, 1512, 1514 having respective axes 1503, 1505, 1507, 1509, 1511, 1513, 1515 can define respective sets of diffusers that are situated about an optical axis 1520. More or fewer sections can be used, and each section defines two or more diffusers. In some examples, each section defines four diffusers.

In view of the many possible embodiments to which the principles of the disclosed technology may be applied, it should be recognized that the illustrated embodiments are only representative examples and should not be taken as limiting the scope of the technology. We claim as our invention all that comes within the scope and spirit of the appended claims.

We claim:

1. A method of measuring the aerosol asymmetry parameter, comprising:

with a plurality of sensors and diffusers appropriately positioned relative to an optical axis, measuring light forward-scattered and backward-scattered by an aerosol sample; and comparing the amounts of forward-scattered and backward-scattered light to determine the aerosol asymmetry parameter.

2. The method of claim 1, wherein measuring light forward-scattered and backward-scattered by the sample comprises detecting light received by a plurality of diffusers, each of the plurality of diffusers having an outer surface with a cross section at least generally corresponding to a quadrant of a circle, wherein the outer surface of each diffuser admits light to a respective sensor.

3. The method of claim 2, wherein the outer surfaces of the diffusers are contiguous.

4. The method of claim 2, wherein two of the diffusers have outer surfaces directed towards the optical axis and two of the diffusers have outer surfaces directed away from the optical axis.

5. The method of claim 4, wherein the two diffusers having an outer surface directed towards the optical axis measure forward-scattering and backward-scattering, one of the diffusers having an outer surface directed away from the optical axis measures forward-scattering, and one of the diffusers having an outer surface directed away from the optical axis measures backward-scattering.

6. The method of claim 4, wherein the two diffusers having an outer surface directed towards the optical axis measure forward-scattering and backward-scattering and generate signals designated $s_1$ and $s_2$, respectively, one of the diffusers having an outer surface directed away from the optical axis measures forward-scattering and generates a signal designated $s_3$, and one of the diffusers having an outer surface directed away from the optical axis measures backward-scattering and generates a signal designated $s_4$ and wherein comparing the amounts of forward-scattered and backward-scattered light to determine the aerosol asymmetry parameter, $g_{retr}$, comprises determining:

$$g_{retr} = k \frac{(s_1 - s_2 + s_3 - s_4)}{(s_1 + s_2 - s_3 - s_4)}$$

where k is a proportionality constant.

7. The method of claim 6, wherein the proportionality constant is $$\frac{1.165}{4\pi}.$$

8. The method of claim 4, wherein the two diffusers having an outer surface directed towards the optical axis measure forward-scattering and backward-scattering and generate signals designated $s_1$ and $s_2$, respectively, one of the diffusers having an outer surface directed away from the optical axis measures forward-scattering and generates a signal designated $s_3$, and one of the diffusers having an outer surface directed away from the optical axis measures backward-scattering and generates a signal designated $s_4$ and wherein comparing the amounts of forward-scattered and backward-scattered light comprises determining a raw detector signal $s_{raw}$, as:

$$s_{raw} = \frac{(s_1 - s_2 + s_3 - s_4)}{2\pi(s_1 + s_2 - s_3 - s_4)}.$$

9. An apparatus useable to measure the aerosol asymmetry parameter comprising a plurality of diffusers and light sensors, the diffusers having outer surfaces with an at least generally circular cross section that admit light to a respective light sensor, the light sensors allowing forward and backward scattering of light to be measured, at least two of the plurality of diffusers positioned such that their outer surfaces are directed towards an optical axis and at least two of the plurality of diffusers positioned such that their outer surfaces are directed away from the optical axis.

10. The apparatus of claim 9, further comprising a housing, the diffusers being disposed inside the housing.

11. The apparatus of claim 10, wherein the housing defines an optical inlet and the optical inlet defines the optical axis.

12. The apparatus of claim 11, wherein the housing defines an optical outlet and the optical axis is defined between the optical inlet and the optical outlet.

13. The apparatus of claim 9, wherein the diffuser outer surfaces are contiguous.

14. The apparatus of claim 9, wherein the plurality of diffusers are arranged in a toroid about the optical axis.

15. The apparatus of claim 9, further comprising at least one optical barrier coupled to each of the plurality of diffusers so that the diffusers are at least substantially optically isolated from each other.

16. The apparatus of claim 9, further comprising a light source.

17. The apparatus of claim 13, wherein the light source comprises a laser.

18. An apparatus useable to measure the aerosol asymmetry parameter, comprising a plurality of diffusers and light sensors positioned relative to an optical axis such that forward scattering and backward scattering of light by an aerosol are measurable, each diffuser admitting light to a respective light sensor.

19. The apparatus of claim 18, further comprising a housing, the plurality of diffusers and light sensors positioned in the housing, and wherein the housing defines an optical inlet that defines the optical axis.

20. The apparatus of claim 19, wherein the housing defines an optical outlet and the optical axis is defined between the optical inlet and the optical outlet.

21. The method of claim 1, wherein forward-scattered and backward-scattered light are simultaneously measured.

22. The apparatus of claim 9, wherein the diffusers and light sensors are configured to allow forward and backward scattering of light to be measured simultaneously.

23. The apparatus of claim 18, wherein the plurality of diffusers and lights sensors are positioned relative to an optical axis such that forward scattering and backward scattering of light by an aerosol are simultaneously measureable.

* * * * *